US008811890B2

(12) United States Patent
Hsueh et al.

(10) Patent No.: US 8,811,890 B2
(45) Date of Patent: Aug. 19, 2014

(54) HOPPING WIRELESS MEDICAL CARE AND MONITORING DEVICE AND METHOD OF OPERATION

(75) Inventors: Ya-Hsin Hsueh, Yunlin (TW); Chih-Yung Wu, Yunlin (TW); Fong-I Jhou, Yunlin (TW)

(73) Assignee: National Yunlin University of Science & Technology, Yunlin (TW)

( * ) Notice: Subject to any disclaimer, the term of this patent is extended or adjusted under 35 U.S.C. 154(b) by 559 days.

(21) Appl. No.: 13/103,151

(22) Filed: May 9, 2011

(65) Prior Publication Data
US 2012/0289149 A1 Nov. 15, 2012

(51) Int. Cl.
*H04B 7/14* (2006.01)
*H04L 29/08* (2006.01)
*A61B 5/00* (2006.01)

(52) U.S. Cl.
CPC ............. *H04L 67/12* (2013.01); *A61B 5/0015* (2013.01)
USPC .......................................................... 455/15

(58) Field of Classification Search
CPC ........................................................ H04B 7/14
USPC ............................................................ 455/15
See application file for complete search history.

(56) References Cited

U.S. PATENT DOCUMENTS

2011/0009727 A1* 1/2011 Mensinger et al. ............ 600/365
2011/0320130 A1* 12/2011 Valdes et al. .................... 702/19

* cited by examiner

*Primary Examiner* — Bobbak Safaipour
(74) *Attorney, Agent, or Firm* — Alan Kamrath; Kamrath IP Lawfirm, P.A.

(57) ABSTRACT

A hopping wireless medical caring and monitoring system, which is an ANT multiple nodes hopping network, includes at least one hopping node, at least one physical status measuring apparatus, a server and at least one user-end apparatus. The server communicates with the at least one user-end apparatus via the ANT network. The user-end apparatus reads a medical measurement result from the physical status measuring apparatus and transmits the results to the server via the ANT network. The wireless remote health and medical caring and monitoring system is suitable for home-care or a hospital.

10 Claims, 5 Drawing Sheets

HOPPING WIRELESS MEDICAL CARE AND MONITORING DEVICE AND METHOD OF OPERATION

FIELD OF THE INVENTION

The present invention relates to a care and monitoring device and, especially, to a hopping wireless medical care and monitoring device suitable for use at home or in a hospital and its method of operation.

BACKGROUND OF THE INVENTION

Improved medical care is resulting in an aging population. Recent developments in communication and wireless technology resulting in remote medical care systems are an important field for markets, industries and research centers. Many related medical care products have been studied and developed.

Most wireless medical care monitoring uses one-way communication, which is passive communication equipment that connects to a wireless station, that transmits signals continuously and that must have a base station for operation. Consequently, wireless signal transmission is very inconvenient.

Therefore, the need for a system and method to provide more efficient signal transmission for a patient's medical monitoring devices still exists.

SUMMARY OF THE INVENTION

The present invention relates to a wireless medical care system using hopping communication and allowing multiple users to access their medical information without any limitation of distance.

According to the present invention, a wireless hopping node medical care monitoring system that is ANT multiple hopping nodes comprises at least one hopping node, at least one physical status measuring apparatus, a server, a network and at least one end-user apparatus. The at least one hopping node forms at least one channel to transmit a wireless signal. ANT is an open access multicast wireless sensor network technology protocol. The at least one physical status measuring apparatus is used to detect a patient's physical status. The server is connected to the at least one hopping node and the network topology for receiving signals, or transmitting a measuring data or an alarm in the wireless signal form through the multiple hopping node network system. The at least one user-end apparatus is connected to the physical status measuring apparatus for reading a physical status data and transmitting the physical status data in wireless form from the at least one hopping node to the server. Each user-end apparatus also receives a wireless signal from another hopping node to output an alarm according to the instruction of the wireless signal.

In a preferred embodiment, each user-end apparatus comprises:
a central processing unit,
an ANT wireless network unit electrically connected to the central processing unit for transmitting signals between the at least one hopping node in a bi-direction pathway,
a physical input signal unit electrically connected to the central processing unit,
an alarm output signal unit electrically connected to the central processing unit,
a monitoring unit electrically connected to the central processing unit, an input interface, and
a real-time timer unit electrically connected to the central processing unit, wherein:
the central processing unit reads the physical measuring data from the physical input signal unit for outputting a wireless signal through the ANT wireless network unit and then transmitting the wireless signal to the server;
the alarm output signal unit receives the wireless signal from the central processing unit;
the monitoring unit shows the wireless signal from the central processing unit.

In a preferred embodiment, each hopping node further comprises:
a hopping micro processing unit, and
a hopping wireless transmitting unit electrically connected to the hopping micro processing unit, wherein the hopping wireless transmitting unit carries out a wireless signal transmission under the ANT network system.

In a preferred embodiment, each hopping node follows a channel argument and the network topology for transmitting a wireless signal, and the channel argument comprises a hopping number, radio frequency, channel number, channel identification, channel period and channel type.

In a preferred embodiment, the network topology for each hopping node is a master line network topology or a slave line network topology, and the channel comprises:
a receiving channel,
a transmitting channel,
a user channel for transmitting a wireless signal to the user-end apparatus, and
a reserved channel for when a failure hopping node occurs.

In a preferred embodiment, the hopping nodes for building the served channel prevents another hopping node from building a new reserved channel by a broadcast signal.

A method for transmitting a wireless medical care system comprises:
setting a multiple hopping node system under an ANT network system comprising:
a server,
multiple hopping nodes, and
a user-end apparatus,
forming a communicating channel following a network topology for building the channel automatically, and
transmitting a wireless signal between the user-end apparatus and the server by the channel, with the wireless signal including a physical measuring data or an alarm.

In a preferred embodiment, forming the communication channel further comprises automatically forming a reserved channel when a failure hopping node is occurs.

In a preferred embodiment, the physical measuring data is read from the user-end apparatus and is transmitted in the wireless signal at the wireless signal transmitting.

In a preferred embodiment, the server transmits the physical measuring data or an alarm to the user-end apparatus.

As the skilled artisan will appreciate, any such method may be modified according to the needs of experiments.

DETAILED DESCRIPTION OF THE INVENTION

The present invention is a wireless hopping node medical care monitoring device and a method of operating the device. The following descriptions of preferred embodiments of this invention are presented for purposes of illustration and description only and are not intended to be exhaustive or to be limiting to the precise form disclosed.

Figure 1:
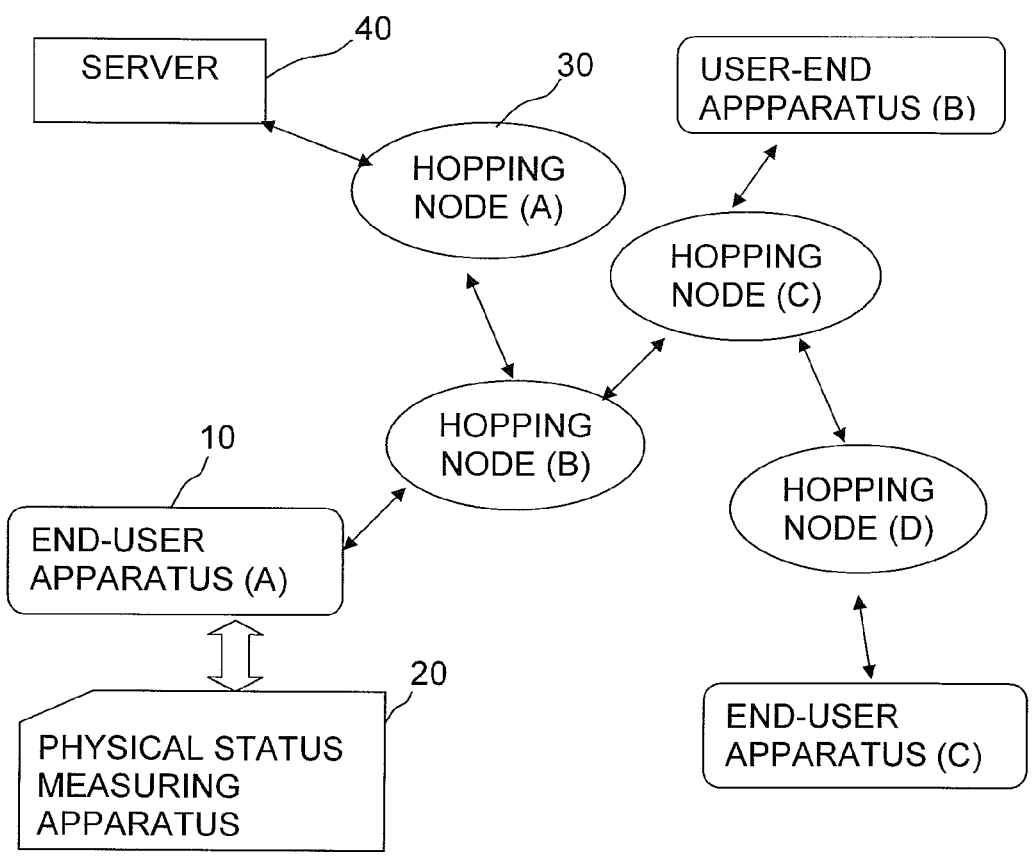
FIG. 1 is a functional block diagram of a preferred embodiment of a wireless hopping node medical care monitoring device in accordance with the present invention.

With reference to FIG. 1, a preferred embodiment of a wireless hopping node medical care monitoring device is an ANT multiple node hopping network and comprises at least one end-user apparatus (10), at least one physical status measuring apparatus (20), at least one hopping node (30) and a server (40). In the multiple nodes hopping network, one of the hopping nodes (30) is used as a relay and the at least one user-end apparatus (10) and the server (40) may be the source or the destination when transmitting a package from a source to a destination.

The multiple node hopping network can be used in any building and will not be limited by range of wireless waves. For example, the multiple nodes hopping network may be used in large hospitals for medical care, sanatoriums or homes. Different types of hopping nodes (30) may be used depending on the need required. The signal may be transmitted farther and continuously.

Figure 2:
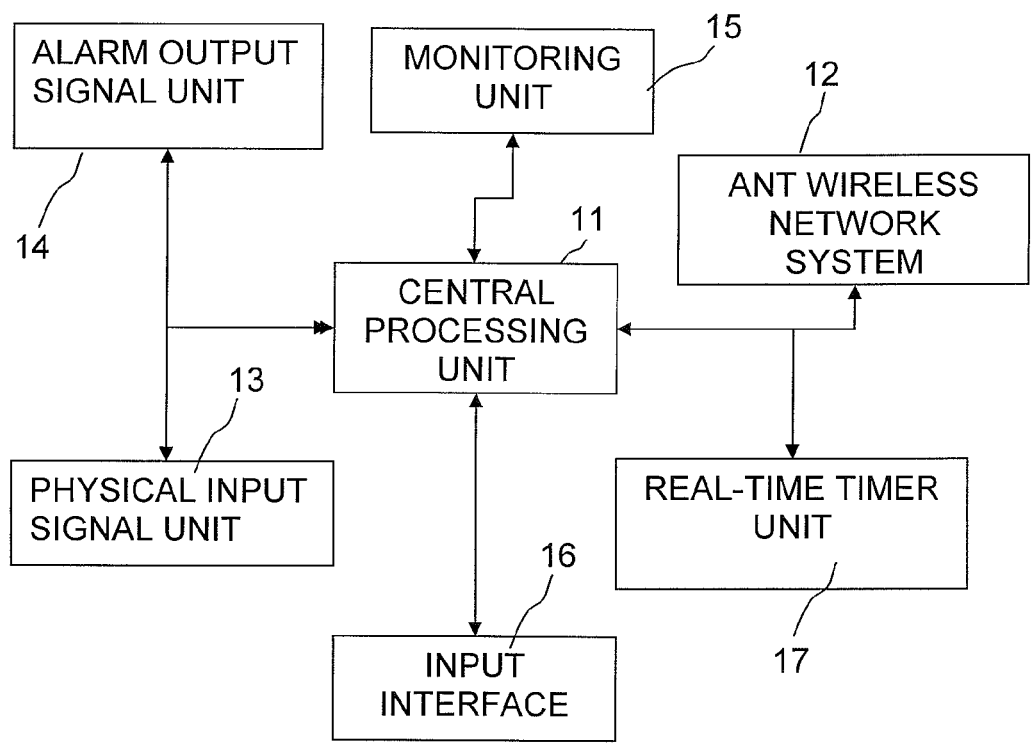
FIG. 2 is a functional block diagram of a preferred embodiment of an end-user apparatus in accordance with the present invention.

With further reference to FIG. 2, each end-user apparatus (10) in accordance with the present invention may comprise a central processing unit (11), an ANT wireless transmission unit (12), a physical input signal unit (13), an alarm output signal unit (14), a monitoring unit (15), an input interface (16) and a real-time timer unit (17). The central processing unit (11) connects bidirectionally to each hopping node (30) by the ANT wireless transmit unit (12) connects to the central processing unit (11) to allow a bidirectional signal transmission. When the ANT wireless transmit unit (12) receives an input wireless signal from one of the hopping nodes (30), the central processing unit (11) will output an alarm signal to control the alarm output signal unit (14), the monitoring unit (15) or the real-time timer unit (17). For example, the input signal may be a drug-taking alarm signal, a physical measuring alarm signal, a real-time signal or a barrier alarm signal. The central processing unit (11) controls the alarm output signal unit (14), a monitoring unit (15) or the real-time timer unit (17) according to the different input signals. The results are shown on a monitoring unit (15), or the alarm output signal unit (14) may show results from the central processing unit (11).

The ANT wireless transmit unit (12) may receive a signal from the central processing unit (11) and transmits a signal to one of the hopping nodes (30), so that the signal could be transmitted by any hopping node (30) to the server (40).

The physical input signal unit (13) may be an electrical signal connecting interface selected from a group but not limited to a USB, RS232 or any kind of wireless transmission interface comprising Bluetooth or infrared ray technology. The physical input signal unit (13) is electrically connected to and reads data from one of the physical status measuring apparatuses (20) and then transmits data to the central processing unit (11). The central processing unit (11) then transmits the data read from the physical status measuring apparatus (20) by the multiple hopping network system.

The alarm output signal unit (14) may be any electrical component with alarm functions including flashing or buzzing. The monitoring unit (15) may be a monitor or a LED monitor controlled by the central processing unit (11). The input interface (16) may be a human-computer interface installed in the end-user apparatus (10). The real-time timer unit (17) may be an electrical component with timer functions.

Each physical status measuring apparatus (20) may be an electrical detecting device for physical status measuring, such as an electrical hemadynamometer, an oximeter or a blood sugar machine. The physical status measuring apparatus (20) is electrically connected to the physical input signal unit (13) and transmits data to the central processing unit (11) to be stored.

Each hopping node (30) meets the requirements of the ANT network, and all the hopping nodes (30) communicate with the end-user apparatus (10) and each other through the ANT network. The hopping nodes (30) comprise a hopping microprocessing unit and a wireless hopping transmitting unit electrically connected to the hopping microprocessing unit. The hopping microprocessing unit controls the transmission and reception of wireless signals from the wireless hopping transmitting unit to form a pathway from the end-user apparatus (10).

All hopping nodes (30) are set by the ANT network. Each hopping node (30) may communicate with one of the other hopping nodes (30) or one of the end-user apparatuses (10) respectively through a specific channel. The communication between two points may build on Master and Slave conditions. To enable communicating between the hopping nodes (30) in the ANT network, the method for arranging the specific channels between the hopping nodes (30) comprises setting a channel argument including Network, radio frequency, hopping number, channel number, channel identification, channel type, channel period, data types and data format. Before operating the wireless communication between two hopping nodes (30), the channel argument should be set up. However, a Master hopping node (30) may use different arguments and devices under one channel for the communication.

When the hopping node (30) transmits a signal, it also receives signals from other hopping nodes (30) connected to the end-user apparatus (10) or the server (40). In a preferred embodiment of the present invention, each hopping node (30) is connected to three specific channels and one reserved channel, which functioned function as a receiving channel (Rx Channel, Slave), a transmitting channel (Tx Channel, Master), a patient channel and a reserved channel, respectively. The receiving channel (Rx Channel, Slave) receives a signal from a previous hopping node (30). The transmitting channel (Tx Channel, Master) communicates with a next hopping node (30). The patient channel communicates with the end-user apparatus (10). The reserved channel connects automatically to the network when failure conditions occur. When a hopping node (30) is subjected to failure conditions, the previous hopping node (30) will connect to the reserved channel to build a transmitting channel, and the next hopping node (30) also connects to the reserved channel to build a receiving channel.

The server (40) connects to the hopping nodes (30) and transmits a signal when a drug-taking alarm or a physical alarm signal is output from an end-user apparatus (10), and a first hopping node (A) will receive a signal from the server (40), and the hopping node (A) transmits a signal to check whether the end-user apparatus (A) is included in a network the same as hopping node (A). If the end-user apparatus (A) is not included in the network, the hopping node (A) will transmit the signal to a second hopping node (B). Similarly, the second hopping node (B) would check whether the end-user apparatus (A) is included in a network the same as the second hopping node (B). If the end-user apparatus (A) is included in the same network as the second hopping node (B), the second hopping node (B) will transmit a signal back to the server (40) and the signal will pass all the hopping nodes (30) in this channel for feedback. Further, if an end-user apparatus (10) could not be found in any of the hopping nodes (30) in the network, the signal will be transmitted to the end hopping node (30). The end hopping node (30) will feedback a signal to show that the end-user apparatus (10) is not included in this wireless network.

Each hopping node (30) may receive signals from a server (40) or an end-user apparatus (10) and subsequently may transmit signals following a reserved network topology method. For example, the network topology method and each hopping node (30) will follow a line network topology for data transmission. For instance, a signal will be passed according to the order of the ID number of each hopping node (30), such as A to B to C to D. For example, hopping node C will automatically connect to hopping node B and hopping node D and will build communication channels between hopping node B and hopping node D to avoid interference between communication channels. In accordance with the present invention, a specific argument and multi-function model are set for each communication channel for avoiding each other.

Further, power for the hopping node (30) is supplied from a battery. When the battery is discharged (lower than a threshold), each hopping node (30) will transmit an alarm signal to the server (40) to remind personnel to change the battery.

A method for setting an argument between the receiving channel (Slave) and the transmitting channel (Master) is as follow. For example, the device may comprise five hopping nodes and the Hopping Node IDs are:

(1) hopping node 31: Hopping Node ID=0x31
(2) hopping node 32: Hopping Node ID=0x32
(3) hopping node 33: Hopping Node ID=0x33
(4) hopping node 34: Hopping Node ID=0x34
(5) hopping node 35: Hopping Node ID=0x35

According to the Hopping Node ID, a channel number will be set depending on channel identification. The order between the channel identification and channel number follows. A channel between the server (40) and hopping node 31: Channel number=0, channel identification=0x30. A channel between hopping node 31 and hopping node 32: Channel number=1, channel identification=0x31. A channel between hopping node 32 and hopping node 33: Channel number=0, channel identification=0x32. A channel between hopping node 33 and hopping node 34: Channel number=1, channel identification=0x33. A channel between hopping node 34 and hopping node 35: Channel number=0, channel identification=0x34.

An example of the principle of setting communication follows. When the channel identification is an odd number, the channel number for communicating with a previous hopping node is set as 0, and channel identification=(Hopping Node ID-1); and the channel number for communicating with a following hopping node is set as 0, and channel identification=Hopping Node ID.

When the channel identification is an even number, the channel number for communicating with a previous hopping node is set as 1, and channel identification=(Hopping Node ID-1); and the channel number for communicating with a following hopping node is set as 1, and channel identification=Hopping Node ID.

When a failure of one hopping node (30) is detected, the failed hopping node (30) will transmit a failure signal that comprises a signal for transmitting to a following hopping node to the server (40) for overcoming the failure condition.

Figure 3A:
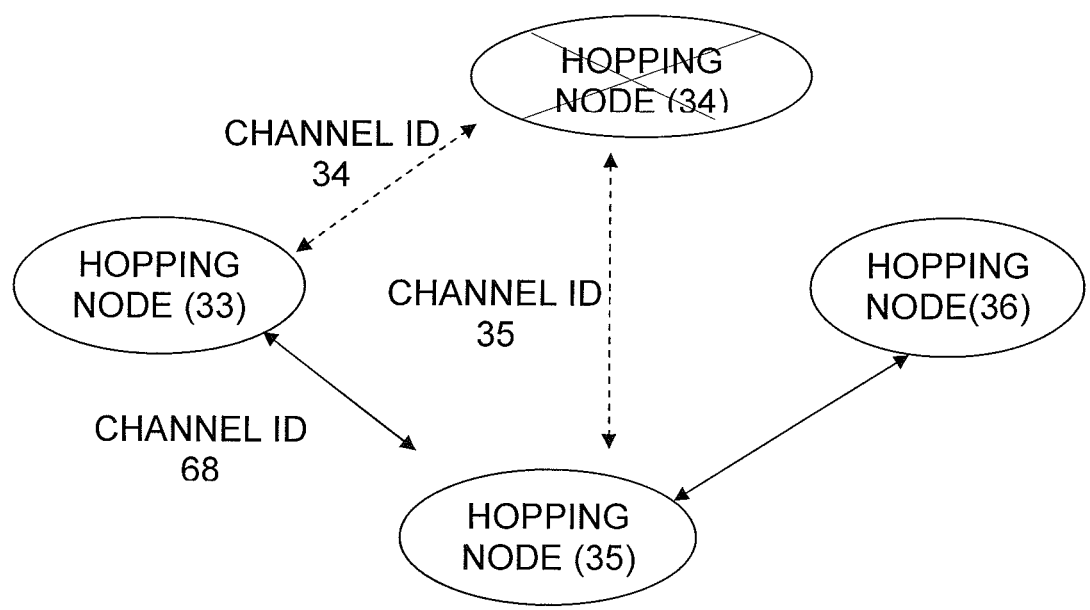
FIGS. 3a to 3c are functional block diagrams of repair conditions in accordance with the present invention.
Figure 3B:
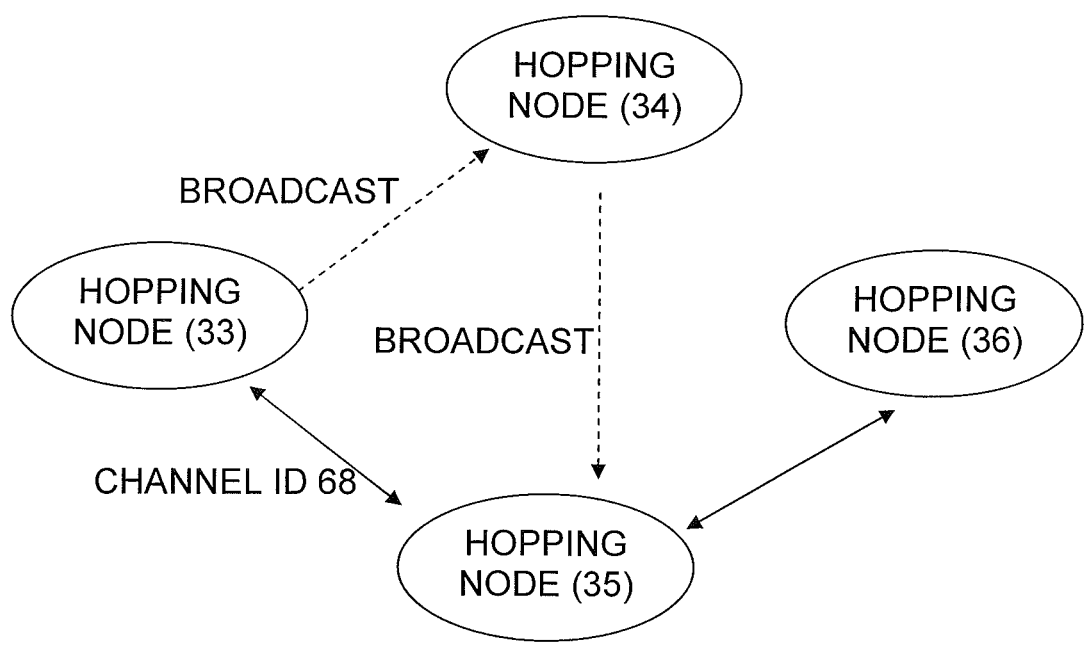
Figure 3C:
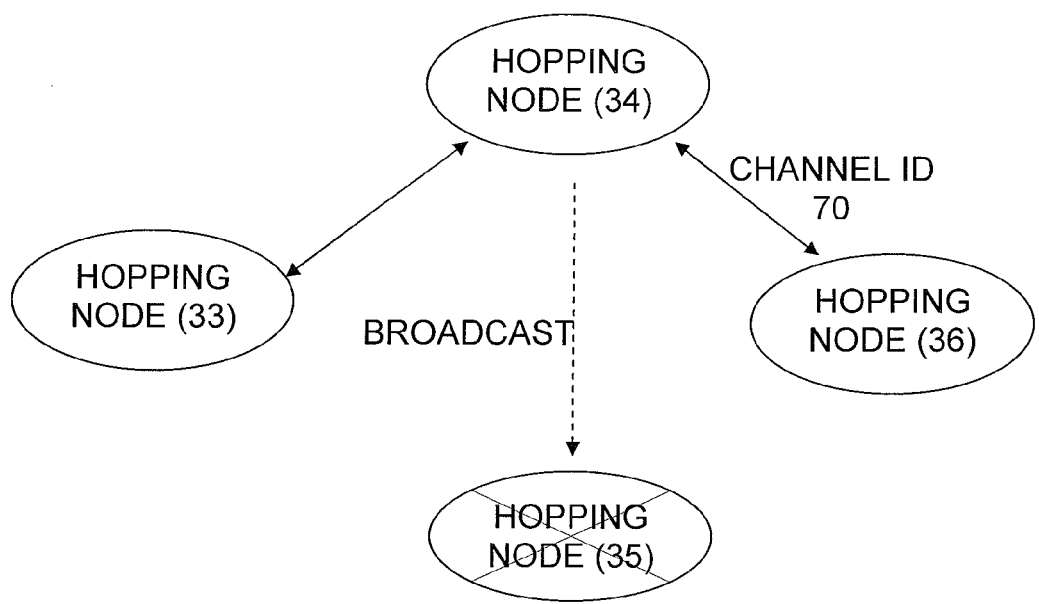

Furthermore, a channel between each hopping node in accordance with the present invention has an automatic repair function. With further reference to FIGS. 3A to 3C, an example is used to illustrate the failure condition and the automatic repair condition.

When a failure condition occurs at a first hopping node (34), the network system formed by multiple hopping nodes is in a breakdown condition. A receiving channel of a second hopping node (35) next to the failed first hopping node (34) could not read any signal. However, after a short period of time (eg. 30 seconds), the second hopping node (35) will connect automatically to a first reserved channel to become a receiving channel (Slave). Until the connection is made, all signal reception will pass the reserved channel. The channel identification (=68) of the first reserved channel becomes a 2-fold change of the failed hopping node (channel RIM identification=34), and a previous hopping node (33) of the failed hopping node (34) transmits a waiting signal and also connects to a second reserved channel to become the transmitting channel (Master). At this time, all data is passed through the first reserved channel and the second reserved channel, and the channel identification of the second reserved channel also becomes a 2-fold change (=68), so that a new transmitting pathway is created and so that the failed hopping node (34) could be ignored for the data transmission. A user or a master user will know the failure condition by the different channel identification or transmitting pathway, and repair the failed hopping nodes. Therefore, when a failure condition occurring in any single hopping node will not breakdown data transmission or the transmitting pathway.

After repairing the pathway with a failed hopping node (34), a previous hopping node of the failed hopping node will transmit a broadcast signal to close the receiving channel (Slave).

When a second failed hopping node (35) occurs, the previous hopping node (33) will follow the model as previously described and transmit a signal to the repaired hopping node (34). The transmitting pathway will be changed as the repaired hopping node (34) transmits to a following hopping node (36).

To conclude, the wireless hopping node medical care and monitoring device in accordance with the present invention comprises a server (40), at least one end-user apparatus (10) and at least one hopping node (30) for wireless transmission of data.

The method for data transmission comprises the steps of (1) building a multiple hopping nodes network, (2) automatically forming communicating channels, and (3) transmitting a wireless signal. Step 1 of building a multiple hopping nodes network comprises building a network under an ANT network. The ANT network comprises a server (40), multiple hopping nodes (30) and at least one end-user apparatus (10). Step 2 of automatically forming communicating channels comprises forming channels between adjacent hopping nodes (30) to form a network topology. Step 3 of transmitting a wireless signal comprises transmitting a wireless signal between the end-user apparatuses (10), the server (40) and the hopping nodes (30). The wireless signal comprises physical measuring data and a medical alarm signal.

In step 2, when one of the hopping nodes (30) fails, adjacent hopping nodes, i.e. the previous one and the next one, will create a reserved channel after a short waiting period.

In step 3, first physical measuring data is read from a physical status measuring apparatus (20) of the end-user apparatus (10), and the data will transform to a wireless signal transmitted between the multiple hopping nodes, and the network to the server (40). Then, the server (40) passes second physical measuring data or the medical alarm signal to the end-user apparatus (10) to allow a person to read the second physical measuring data or the alarm signal.

The device in accordance with the present invention is not to be limited in scope by the specific embodiments described in the detailed description. Various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

The invention claimed is:

1. A wireless hopping node medical care monitoring device is an ANT multiple hopping nodes network comprising:
   at least one physical status measuring apparatus;
   at least one hopping node forming at least one channel transmitting a wireless signal following a network topology to form a multiple hopping node network system, wherein the network topology for each hopping node is a master line network topology or a slave line network topology, and wherein the channel comprises:
      a receiving channel,
      a transmitting channel,
      a user channel, and
      a reserved channel when a failure hopping node occurs;
   at least one physical status measuring apparatus for detecting a patient's physical status;
   a server connected to the at least one hopping node and the network topology for receiving a wireless signal, or transmitting a measuring data or an alarm in a wireless signal form through the multiple hopping nodes network; and
   at least one end-user apparatus connected to the at least one physical status measuring apparatus for reading physical status data and transmitting the physical status data in wireless form from the at least one hopping node to the server, with the user channel transmitting the wireless signal to the at least one end-user apparatus, with each end-user apparatus also receiving a wireless signal from another hopping node to output an alarm according to instructions of the wireless signal.

2. The device according to claim 1, wherein each end-user apparatus comprises:
   a central processing unit,
   an ANT wireless network unit electrically connected to the central processing unit and transmitting signals between the at least one hopping node in a bi-direction pathway,
   a physical input signal unit electrically connected to the central processing unit,
   an alarm output signal unit electrically connected to the central processing unit,
   a monitoring unit electrically connected to the central processing unit,
   an input interface, and
   a real-time timer unit electrically connected to the central processing unit, and wherein:
      the central processing unit reads the physical measuring data from the physical input signal unit and outputting the wireless signal through the ANT wireless network unit and then transmitting the wireless signal to the server;
      the alarm output signal unit receives the wireless signal from the central processing unit; and
      the monitoring unit shows the wireless signal from the central processing unit.

3. The device according to claim 2 wherein each hopping node further comprises:
   a hopping microprocessing unit, and
   a hopping wireless transmitting unit electrically connected to the hopping microprocessing unit, wherein the hopping wireless transmitting unit transmits the wireless signal under the ANT network system unit.

4. The device according to claim 3, wherein each hopping node follows a channel argument and the network topology for transmitting the wireless signal, and wherein the channel argument comprises a hopping number, a radio frequency, a channel number, a channel identification, a channel period and a channel type.

5. The device according to claim 1, wherein the failure hopping node of the reserved channel prevents the failure hopping node from building a new reserved channel by a broadcast signal.

6. A method for transmitting a wireless medical caring system, comprising:
   setting a multiple hopping node system under an ANT network system comprising:
      a server,
      multiple hopping nodes, and
      a user-end apparatus;
   forming a communication channel following a network topology for building the communicating channel automatically and automatically forming a reserved channel when a failure hopping node occurs, wherein the network topology is a master line network topology on a slave line network topology; and
   transmitting a wireless signal between the user-end apparatus and the server by the communicating channel, with the wireless signal including a physical measuring data or an alarm.

7. The method according to claim 6, wherein the physical measuring data is read from the user-end apparatus and transmitted in the wireless signal at the wireless signal transmitting.

8. The method according to claim 7, wherein the server transmits the physical measuring data or the alarm to the user-end apparatus.

9. The method according to claim 6, wherein the server transmits the physical measuring data or the alarm to the user-end apparatus.

10. The method according to claim 9, wherein the physical measuring data is read from the user-end apparatus and transmitted in the wireless signal at the wireless signal transmitting.

* * * * *